US012631772B2

(12) United States Patent
Sirkis et al.

(10) Patent No.: US 12,631,772 B2
(45) Date of Patent: May 19, 2026

(54) SOIL RIPPER WITH GAMMA DETECTOR AND METHOD OF USE TO DETECT CONTAMINATED SOILS

(71) Applicant: United States of America as Represented by The Secretary of the Army, Alexandria, VA (US)

(72) Inventors: Daniel M. Sirkis, Morrisville, PA (US); Steven D. Glazier, Thornton, PA (US); James A. Ambler, Abingdon, MD (US)

(*) Notice: Subject to any disclaimer, the term of this patent is extended or adjusted under 35 U.S.C. 154(b) by 300 days.

(21) Appl. No.: 18/374,946

(22) Filed: Sep. 29, 2023

(65) Prior Publication Data

US 2024/0418872 A1 Dec. 19, 2024

Related U.S. Application Data

(60) Provisional application No. 63/521,097, filed on Jun. 15, 2023.

(51) Int. Cl.
| | |
|---|---|
| *G01T 1/167* | (2006.01) |
| *G01N 33/24* | (2006.01) |
| *G01T 1/169* | (2006.01) |

(52) U.S. Cl.
CPC .............. *G01T 1/167* (2013.01); *G01T 1/169* (2013.01); *G01N 33/24* (2013.01)

(58) Field of Classification Search
CPC .......... G01T 1/167; G01T 1/169; G01N 33/24
See application file for complete search history.

(56) References Cited

FOREIGN PATENT DOCUMENTS

| | | | | |
|---|---|---|---|---|
| RU | 2008734 C1 | * | 2/1994 | |
| WO | WO-2018118716 A1 | * | 6/2018 | ........... G01N 21/474 |
| WO | WO-2021214557 A1 | * | 10/2021 | ............. G01N 33/24 |

* cited by examiner

*Primary Examiner* — David J Makiya
*Assistant Examiner* — Fani Polyzos Boosalis

(57) ABSTRACT

In one embodiment, contamination detection includes attaching a front-facing side of a detector enclosure to a ripper of a ripper machine. The detector enclosure includes a rear-facing side having a rear-facing window, two lateral-facing sides, and a bottom-facing side. A detector is disposed inside the detector enclosure. The ripper is inserted into a soil to position the rear-facing window, the two lateral-facing sides, and the bottom-facing side of the detector enclosure below a soil surface of the soil. The ripper is moved horizontally through the soil leading with the front-facing side of the detector enclosure to detect subsurface contamination via the rear-facing window using the detector.

20 Claims, 5 Drawing Sheets

300

330
318
340
310
340
314
316
360
320

360
330
350
318
310
312

410

414

400

504

500

550

540

530

550

CROSS-SECTION IDEALIZED SOIL COMPRESSION FROM JAAC MOVEMENT

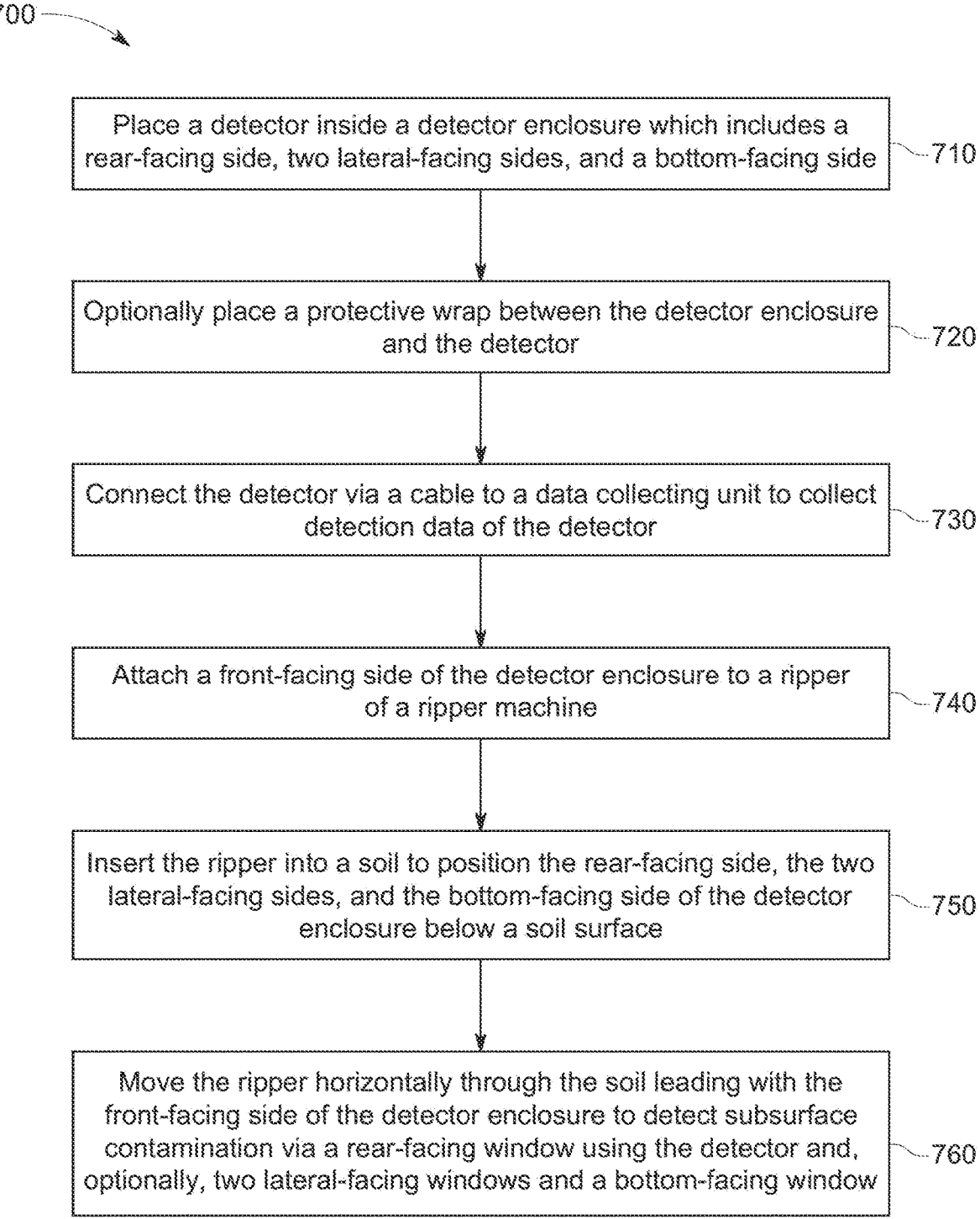

700

Place a detector inside a detector enclosure which includes a rear-facing side, two lateral-facing sides, and a bottom-facing side ~710

Optionally place a protective wrap between the detector enclosure and the detector ~720

Connect the detector via a cable to a data collecting unit to collect detection data of the detector ~730

Attach a front-facing side of the detector enclosure to a ripper of a ripper machine ~740

Insert the ripper into a soil to position the rear-facing side, the two lateral-facing sides, and the bottom-facing side of the detector enclosure below a soil surface ~750

Move the ripper horizontally through the soil leading with the front-facing side of the detector enclosure to detect subsurface contamination via a rear-facing window using the detector and, optionally, two lateral-facing windows and a bottom-facing window ~760

FIG. 7

SOIL RIPPER WITH GAMMA DETECTOR AND METHOD OF USE TO DETECT CONTAMINATED SOILS

CROSS-REFERENCE TO RELATED APPLICATIONS

The application claims the benefit of priority from U.S. Provisional Patent Application No. 63/521,097, filed on Jun. 15, 2023, entitled SOIL RIPPER WITH GAMMA DETECTOR AND METHOD OF USE TO DETECT CONTAMINATED SOILS, the disclosure of which is incorporated by reference in its entirety.

STATEMENT OF GOVERNMENT INTEREST

Under paragraph 1 (a) of Executive Order 10096, the conditions under which this invention was made entitle the Government of the United States, as represented by the Secretary of the Army, to an undivided interest therein on any patent granted thereon by the United States. This and related patents are available for licensing to qualified licensees.

BACKGROUND

Field of the Invention

The present invention relates to detection of contaminated soils and, more specifically, to apparatuses and methods for subsurface radiation detection of soils.

Description of the Related Art

This section introduces aspects that may help facilitate a better understanding of the invention. Accordingly, the statements of this section are to be read in this light and are not to be understood as admissions about what is prior art or what is not prior art.

The current state-of-the-art methodology for screening subsurface soil for radiation is limited to gamma surveys which can be accomplished by walking, driving, or flying gamma detectors over the surface of suspect areas and recording the gamma readings along with GPS data. This is generally the first step in any investigation and is followed by hand auguring or test pitting areas that show increased gamma activity for the collection of soil samples. Soil borings are then performed with a drill rig to determine depths of contamination.

Detection depths for gamma walkovers vary according to particle energy, and soil properties. On average, current instruments can detect gamma radiation from processed uranium contamination at a maximum depth of about 16-45 cm below ground surface. For sites where buried radioactive soil or debris exist, the current state-of-the-art for subsurface detection is ineffective because thin layers of topsoil or cover material (e.g., asphalt, crushed stone, etc.) can easily mask the radiological signature from buried radioactive debris.

SUMMARY

The present invention was developed to address the desire for detection of deeper subsurface contamination detection. A subsurface screening system employs a combination of a gamma detector and a rock ripper which together are called the Joint Activity Acquisition Cutlass (JAAC). The JAAC allows existing detectors to screen for buried radioactive soil or debris at greater depths. This is done by attaching a sodium iodide detector about 1 meter below the ground on the trailing edge of a commercially available cutlass known as a ripper attachment or rock ripper. This allows a subsurface gamma detector to be moved through the soil thus exposing a large area of underground soil to the detector without having to excavate or drill.

Embodiments of the invention are directed to subsurface detection, more specifically, contamination detection in soil using a ripper machine having a ripper. A front-facing side of a detector enclosure is attached to the ripper. The detector enclosure includes a rear-facing side having a rear-facing window, two lateral-facing sides, and a bottom-facing side. A detector is disposed inside the detector enclosure. The ripper is inserted into the soil to position the rear-facing window, the two lateral-facing sides, and the bottom-facing side of the detector enclosure below a soil surface of the soil. The ripper is moved horizontally through the soil leading with the front-facing side of the detector enclosure to detect subsurface contamination via the rear-facing window using the detector. The lateral-facing sides may include lateral-facing windows and the bottom-facing side may include a bottom-facing window. These windows provide additional coverage or opportunity for contamination detection by the detector.

According to an aspect the present invention, a contamination detection apparatus for subsurface contamination detection comprises: a detector enclosure including a front-facing side to be attached to a ripper of a ripper machine and a rear-facing side having a rear-facing window, two lateral-facing sides, and a bottom-facing side; and a bottom door at a bottom side of the detector enclosure to move between a closed position and an open position, the bottom door in the closed position supporting a detector to be placed inside the detector enclosure to detect for subsurface contamination via the rear-facing window.

In accordance with another aspect of the invention, a contamination detection method comprises: attaching a front-facing side of a detector enclosure to a ripper of a ripper machine, the detector enclosure including a rear-facing side having a rear-facing window, two lateral-facing sides, and a bottom-facing side; placing a detector inside the detector enclosure; inserting the ripper into a soil to position the rear-facing window, the two lateral-facing sides, and the bottom-facing side of the detector enclosure below a soil surface of the soil; and moving the ripper horizontally through the soil leading with the front-facing side of the detector enclosure to detect subsurface contamination via the rear-facing window using the detector.

In accordance with yet another aspect, a contamination detection apparatus for subsurface contamination detection comprises: a ripper of a ripper machine; and a detector enclosure including a front-facing side to be attached to the ripper of the ripper machine and a rear-facing side having a rear-facing window, two lateral-facing sides, and a bottom-facing side. The rear-facing side of the detector enclosure includes a rear-facing window to facilitate detection, by a detector disposed inside the detector enclosure, for subsurface contamination via the rear-facing window.

BRIEF DESCRIPTION OF THE DRAWINGS

Embodiments of the invention will become more fully apparent from the following detailed description, the appended claims, and the accompanying drawings in which like reference numerals identify similar or identical elements.

FIG. 7 is a flow diagram illustrating an example of a method of subsurface contamination detection.

DETAILED DESCRIPTION

Figure 1:
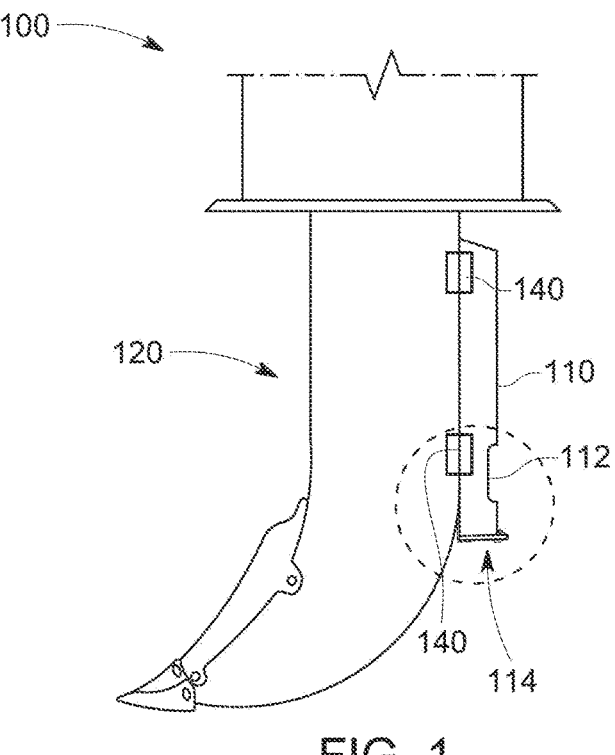
FIG. 1 is a side elevational view illustrating an example of a contamination detection apparatus in the form of a Joint Activity Acquisition Cutlass (JAAC).

Detailed illustrative embodiments of the present invention are disclosed herein. However, specific structural and functional details disclosed herein are merely representative for purposes of describing example embodiments of the present invention. The present invention may be embodied in many alternate forms and should not be construed as limited to only the embodiments set forth herein. Further, the terminology used herein is for the purpose of describing particular embodiments only and is not intended to be limiting of example embodiments of the invention.

As used herein, the singular forms "a," "an," and "the," are intended to include the plural forms as well, unless the context clearly indicates otherwise. It further will be understood that the terms "comprises," "comprising," "includes," and/or "including," specify the presence of stated features, steps, or components, but do not preclude the presence or addition of one or more other features, steps, or components. It also should be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

The JAAC allows existing detectors to screen for buried radioactive soil or debris at greater depths by attaching a sodium iodide detector about 1 meter below the ground on the trailing edge of a rock ripper. Deeper depths are possible with rippers that extend deeper into the subsurface. This will allow the JAAC to survey large areas for deeper contamination minimizing the requirement to dig test pits or drill. At sites where the soil can be contaminated with chemicals, this can be an important innovation by minimizing disturbance of subsurface soils. Drilling is still the best way to vertically delineate contamination, but it can be very expensive and time intensive and is not specifically designed for horizontal delineation. The JAAC is designed to provide a horizontal profile for shallow contamination which can augment or spur follow-on vertical investigations. Investigation at a particular site has found areas where sporadically buried contaminated material results in clean boreholes, but during remediation, the contamination was found well outside of delineated areas defined by drilling. Thus, the need for a better detection system arose and the JAAC was envisioned.

As the JAAC is pulled forward by a dozer or excavator, the ripper compresses the soil on the leading edge, divides the soil on two sides of the ripper, then decompresses and anneals the soil on the trailing edge of the ripper. An important opportunity for detection lies with the decompressed soil behind the ripper's path though other windows in the enclosure also provide detection opportunities. A structural steel square metal box/tube includes rear, side/lateral, and bottom-facing cut-outs or windows and is affixed to the trailing edge of the ripper. Through the rear, side/lateral, and bottom-facing windows, the gamma detector can screen the decompressed soil while being protected from soil, debris, or rocks that move past the detector. The side/lateral and bottom-facing windows can screen for gamma from those directions. Specifically, the detector is installed within the square metal box/tube and the detector cable runs through the metal box/tube which extends above the soil surface allowing the cable and connector to be fully protected. The detector may be cushioned by a protective wrap between the detector and the box/tube. Since the cable and steel box/tube daylight above the soil, the cable can be safely connected to an onboard computer/GPS system located in a location on the excavator arm or the bulldozers bodywork. Through the use of modem wireless communication systems such as Bluetooth, the data can be observed in real time by the operator or technician while also allowing for data logging.

The initial JAAC design allows for an approximate 90 to 120-degree rear-facing angle of gamma detection and the detector will be affixed approximately 1 meter below ground surface. Some foam insulation around the detector may be needed to dampen vibration. It is possible that ruggedized detectors may be needed if vibration dampening is insufficient to ensure detector survivability and data quality. Pilot testing starts with a relatively shallow depth and if proven successful, deeper insertion depths are possible. The addition of side/lateral and bottom windows increases the detection capabilities of JAAC.

The detectors may still be limited to detecting gamma rays within approximately a 0.5-meter radius around the portions of the detector that are unobstructed. However, the JAAC is designed to be pulled by a dozer or trackhoe and will be used similar to a plow. Successive rows can be surveyed with the JAAC thereby providing shallow coverage to large areas in a small period of time. The JAAC is designed to protect the subsurface detector from head-on forces created by moving through soil. It is not designed to counteract lateral forces that may occur from turns made by the dozer/JAAC. As such, the JAAC should be lifted out of the soil prior to turning, and then re-inserted on successive straight runs. If increases in radioactivity are detected by JAAC, since the GPS position associated with that detection is recorded, follow-up test pitting or drilling can be performed at that location.

FIG. 1 is a side elevational view illustrating an example of a contamination detection apparatus 100 in the form of a Joint Activity Acquisition Cutlass (JAAC). The JAAC has a detector enclosure mounted on a ripper for housing or enclosing a contamination detector. The contamination detection apparatus 100 is a subsurface screening system using a combination of a contamination detector in a custom housing and a rock ripper to allow existing detectors to screen for buried contamination. This is done by installing a detector into a custom-designed enclosure 110 which may be a structural steel square metal box/tube with a rear-facing window 112 affixed to the trailing edge of a cutlass known as a ripper attachment or rock ripper 120. The box/tube 110 has an access port 114 on the base to allow installation of a detector.

Figure 2:
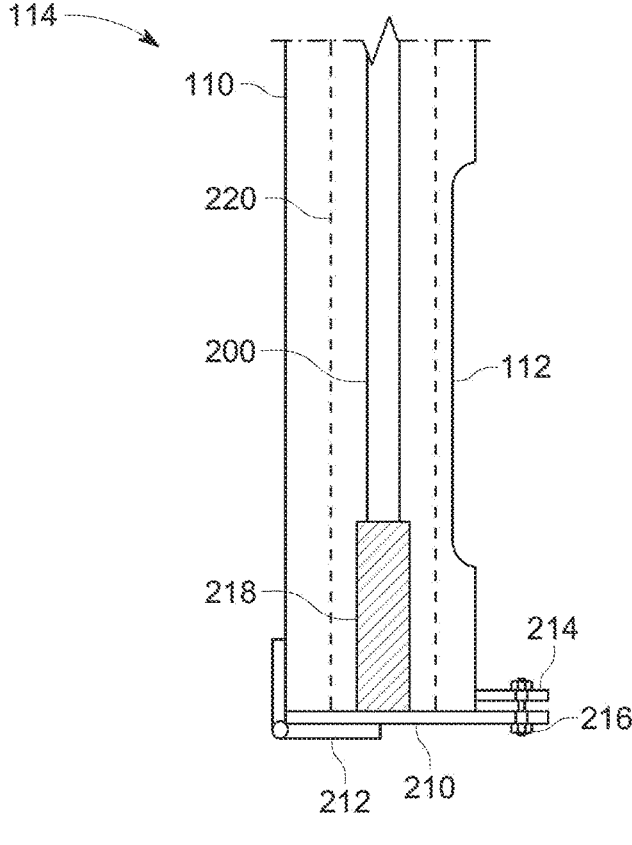
FIG. 2 is a close-up view illustrating a detector disposed in a detector enclosure to be mounted to a ripper of the contamination detection apparatus of FIG. 1.

FIG. 2 illustrates a detector 200 disposed in the detector enclosure 110 to be mounted to the ripper 120 in Detail A of FIG. 1. The detector enclosure 110 may be formed by a square metal box or tube. The box/tube 110 includes the rear-facing window 112 which may be located about 1 meter below the ground on the trailing edge of the ripper 120 but can be placed deeper into the ground with longer rippers. This allows the JAAC 100 to survey large areas for contamination minimizing the requirement to dig test pits or drill which are expensive and create contaminated waste.

The access port 114 includes a bottom plate 210 attached to the box/tube 110 by a hinge 212 to allow the bottom plate 210 to rotatably or hingedly moved between an open position and a closed position. The bottom plate 210 may be held in the closed position by attaching it to a locking plate 214 using a fastener 216 such as a bolt and a nut. The bottom plate 210 may include a bottom support 218 such as a wood dowel extending upward in the interior of the detector enclosure 110 to support the detector 200 at a preset distance from the bottom plate 210. An optional intermediate enclosure 220 may enclose the detector 200 and the bottom support 218. The intermediate enclosure 220 may provide additional protection and support of the detector 200. In specific embodiments, the intermediate enclosure 220 may be a 3-inch diameter HDPE pipe. The enclosure 110 may be a $\frac{3}{16}$-inch square tube of 3"×3" in size. The rear-facing window 112 may be 3'×6" nominal in size at a depth of ½". The locking plate 214 may be a $\frac{3}{16}$-inch plate of 2"×1.5" in size. The bottom plate 210 may be a $\frac{3}{16}$-inch plate of 3.5"×4.5" in size. The hinge 212 may be a 3" steel hinge. The fastener 216 may include a ¼-inch diameter bolt and nut.

The addition of a structural steel square metal box/tube 110 having a rear-facing window 112 and being affixed to the trailing edge of the ripper 120 will allow the detector 200 to screen the decompressed soil while being protected from soil, debris, or rocks that move past the detector 200. Specifically, the detector 200 is installed within the square metal box/tube 110 and the detector cable runs through the metal box/tube 110 which extends above the soil surface allowing the cable and connector to be fully protected.

In one embodiment, the JAAC is configured to hold a standard 2×2 sodium iodide detector and provide access for the detector cable to extend above the ground to a meter mounted on an excavator or a dozer. The detector housing 110 includes the hinged door 210 on the base of the detector 200 and the window 112 through the steel to allow the radiation to enter the enclosure unattenuated by the steel. The detector 200 may be an AR-19 gamma detector and the rear-facing window 112 is a rear-facing cut-out to allow gamma radiation to pass through for gamma radiation detection by the gamma detector. The initial design allows for an approximate 90 to 120-degree rear-facing angle of detection for optical or radiological detectors.

The enclosure 110 may be connected or attached to the trailing edge of the rock ripper 120 using welds or attachment plate 140 or the like, with the rear-facing window 112 facing the opposite direction in which the ripper 120 is pulled through the soil. The hinge 212 is placed on the bottom of the enclosure 110 to allow the detector 200 to be inserted properly into the enclosure 110.

Figure 3A:
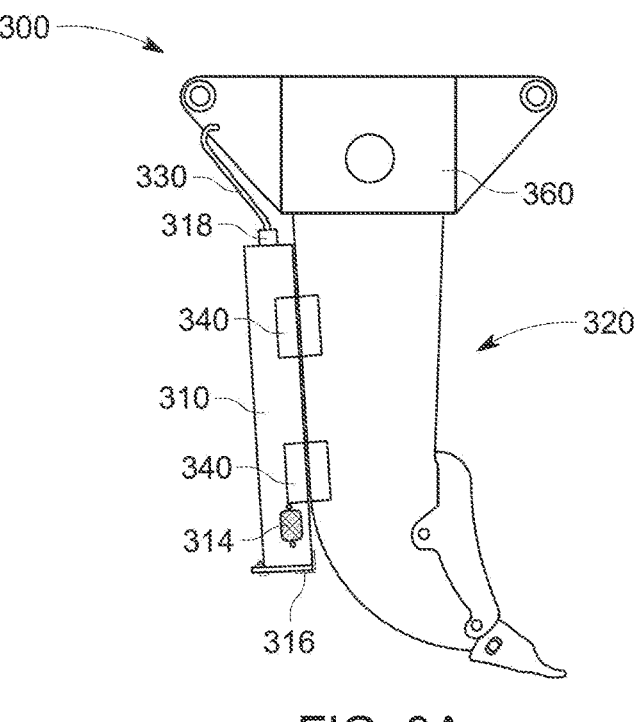
FIG. 3A is a side elevational view illustrating another example of the contamination detection apparatus in the form of a JAAC.
Figure 3B:
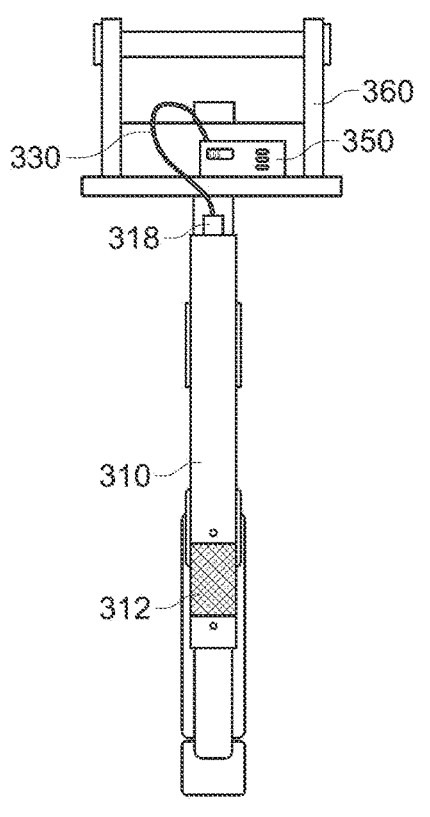
FIG. 3B is a rear elevational view of the contamination detection apparatus of FIG. 3A.

FIG. 3A is a side elevational view illustrating another example of the contamination detection apparatus in the form of a JAAC. FIG. 3B is a rear elevational view of the contamination detection apparatus 300 of FIG. 3A. It is similar to the contamination detection apparatus 100 of FIGS. 1 and 2. The contamination detection apparatus 300 includes additional features.

The contamination detection apparatus 300 in the form of a JAAC has a detector enclosure 310 mounted on a ripper for housing a contamination detector. The contamination detection apparatus 300 includes a contamination detector in a contamination detector housing and a rock ripper to allow the contamination detector to screen for buried contamination. The contamination detector enclosure 310 may be a structural steel square metal box/tube with a rear-facing cut-out or window 312 affixed to the trailing edge of a ripper attachment or rock ripper 320. In addition to the rear-facing cut-out 312, the detector enclosure 310 includes two lateral-facing sides each having a lateral-facing cut-out 314 and a bottom-facing side having a bottom-facing cut-out 316. The box/tube 310 has a nipple 318 welded to the top. The nipple 318 may be made of metal. It allows detector cables 330 to safely become exposed above the soil.

The detector enclosure 310 may be a metal box or tube having the rear-facing cut-out or window 312, two lateral-facing cut-outs or windows 314, and bottom-facing cut-out or window 316. The additional lateral-facing and bottom-facing cut-outs or windows 314, 316 allow the JAAC 300 to survey larger areas on each pass for contamination as compared to the JAAC 100 of FIG. 1 having only the rear-facing cut-out or window 112. The forward movement of the ripper 320 creates a wake behind not only in the rear direction for the rear-facing window 312 but in the bottom-facing window 316 as well. This allows the detector inside the detector enclosure 310 to screen the decompressed soil through the cut-outs or windows 312, and 316 while being protected from soil, debris, or rocks that move past the detector. Window 314 would be open to radiations from the side of the enclosure, but it would be compressed soil. The enclosure 310 may be connected or attached to the trailing edge of the rock ripper 320 using welds or attachment plate 340 or the like, with the window 312 facing the opposite direction in which the ripper 320 is pulled through the soil.

In specific embodiments, the ripper 320 may have a 3-inch thick shaft. The detector enclosure 310 may have a 4-inch square tube. The detector enclosure 310 may be made of a metal such as stainless steel. The nipple 318 may provide a 2-inch steel conduit. The enclosure 310 may be welded to the ripper 320 using four ¼-inch steel plates 340, two on each side. The rear-facing window 312 may be 2"×6" or 3"×6" in size. The lateral-facing windows 314 may each be 2"×3" in size. The bottom-facing window 316 may be _"×_" in size. The windows may be open cut-outs or covered with a polymer or plastic material including a polycarbonate resin thermoplastic, in the form of a plastic sheet or polymer sheet, such as a ¼-inch Lexan sheet. The detector may rest at the bottom of the detector enclosure 310 and optionally wrapped in a protective material, as described below. In other embodiments, the detector enclosure 310 may be made of a polymer such as fiberglass, acrylic, plexiglass, or the like.

In some embodiments, the windows 312, 314, 316 may be open cut-outs to facilitate detection of gamma radiation or the like. The windows may be covered with a material that allows gamma radiation to pass therethrough (e.g., a plastic material including polycarbonate or the like, such as a Lexan polycarbonate sheet). In other embodiments, the windows

312, 314, 316 may be open cut-outs or covered with a material that allows UV light to pass therethrough (e.g., acrylic material). This would be important if the detector was using UV light to find free-phase organic chemicals which fluoresce under UV light. The detector may be a photo-ionization detector (PID) for measuring volatile organic volatile organic compounds (VOCs) and other toxic gasses in low concentrations from ppb (parts per billion) p to 10000 ppm (parts per million) in which case a gas permeable window would be required.

With the detector installed within the detector enclosure box/tube 310, the detector cable 330 runs through the detector enclosure box/tube which extends above the soil surface allowing the cable 330 and connector to be fully protected. Since the cable 330 and steel box/tube 310 daylight above the soil, the cable 330 can be safely connected to an onboard computer/GPS system 350 located in a basket or the like on the excavator arm or the bulldozers bodywork 360. The computer/GPS system 350 serves as a data collecting unit to collect subsurface contamination detection data of the detector along with location data. Through the use of wireless communication systems such as Bluetooth®, the data can be observed in real-time by the operator and technician while also allowing for data logging.

Figure 4:
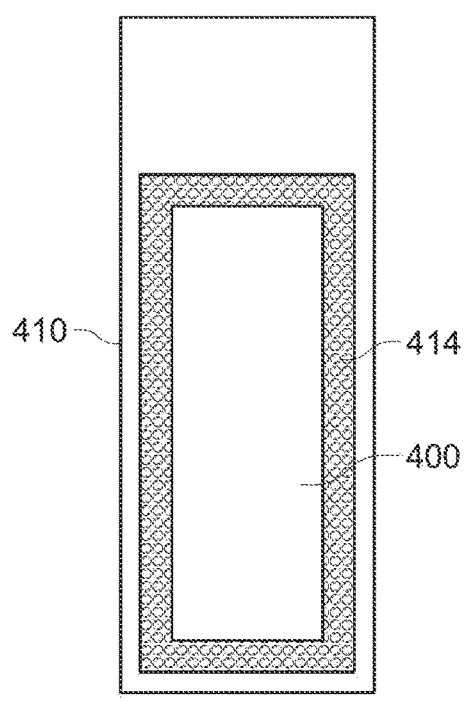
FIG. 4 is a schematic plan view of a contamination detection apparatus in the form of a JAAC being pulled forward by a machine or vehicle such as a dozer or an excavator to compress and divide the soil, illustrating different soil zones.

FIG. 4 is a schematic sectional view of a detector 400 disposed in a detector enclosure 410 illustrating a protective wrap 414 according to an embodiment. The detector 400 is cushioned by the protective wrap 414 such as a bubble wrap or foam insulation between the detector 400 and the box/tube 410. The protective wrap 414 around the detector 400 dampens vibration to protect the integrity, survivability, and data quality of the detector 400. Initial tests showed surprisingly low stress within the enclosure 410 with the protective bubble wrap 414. Alternatively, a ruggedized detector may be used without a protective wrap or other vibration dampening mechanism.

Figure 5:
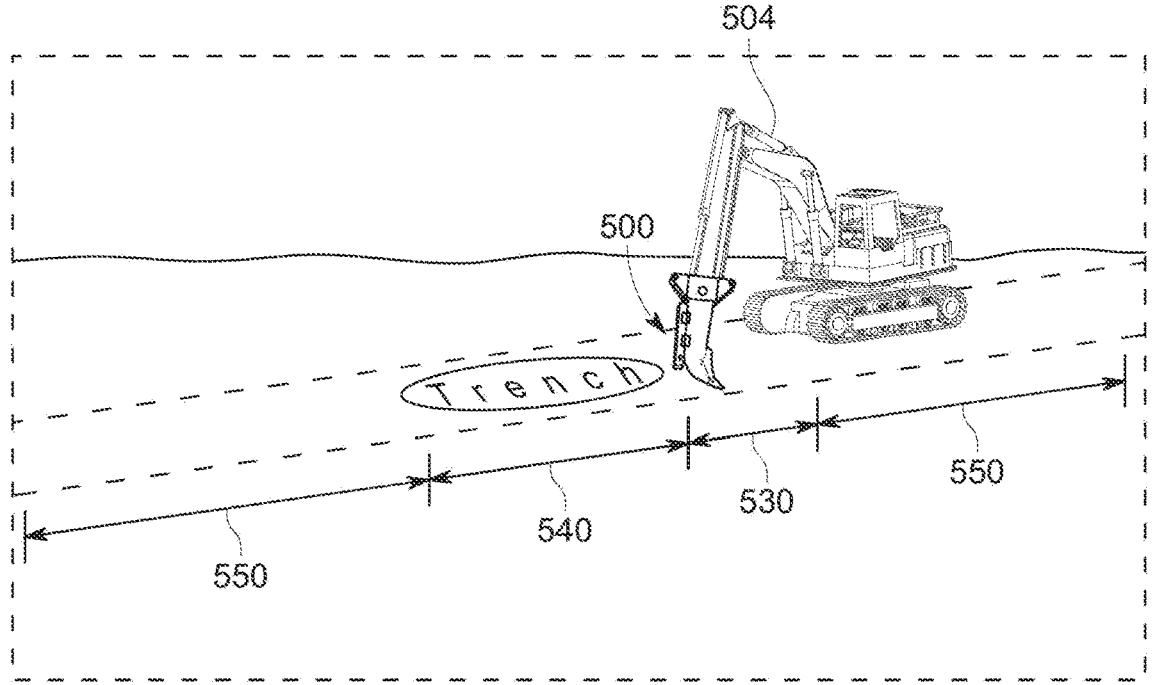
FIG. 5 is a schematic cross-sectional view of the different soil zones of FIG. 4 as a result of pulling the JAAC through the soil.

FIG. 5 is a schematic plan view of a JAAC 500 being pulled forward by a machine or vehicle 504 such as a dozer or an excavator to compress and divide the soil, illustrating different soil zones. As the JAAC 500 is pulled forward by the machine 504, the ripper 520 compresses the soil on the leading edge, divides the soil which then flows on both the sides of the ripper 520. A compressed zone 530 is formed between the ripper 520 and the machine 504 as the machine 504 pulls the ripper 520 in forward motion to compress the soil. A decompressed zone 540 is formed behind the ripper 520 after the ripper 520 divides the soil. Normal density zones 550 not affected by the ripper 520 are disposed behind the decompressed zone 540 and in front of the compressed zone 530. The ripper 520 forms a trench in its wake after compressing the soil and dividing the soil to decompress it.

Figure 6:
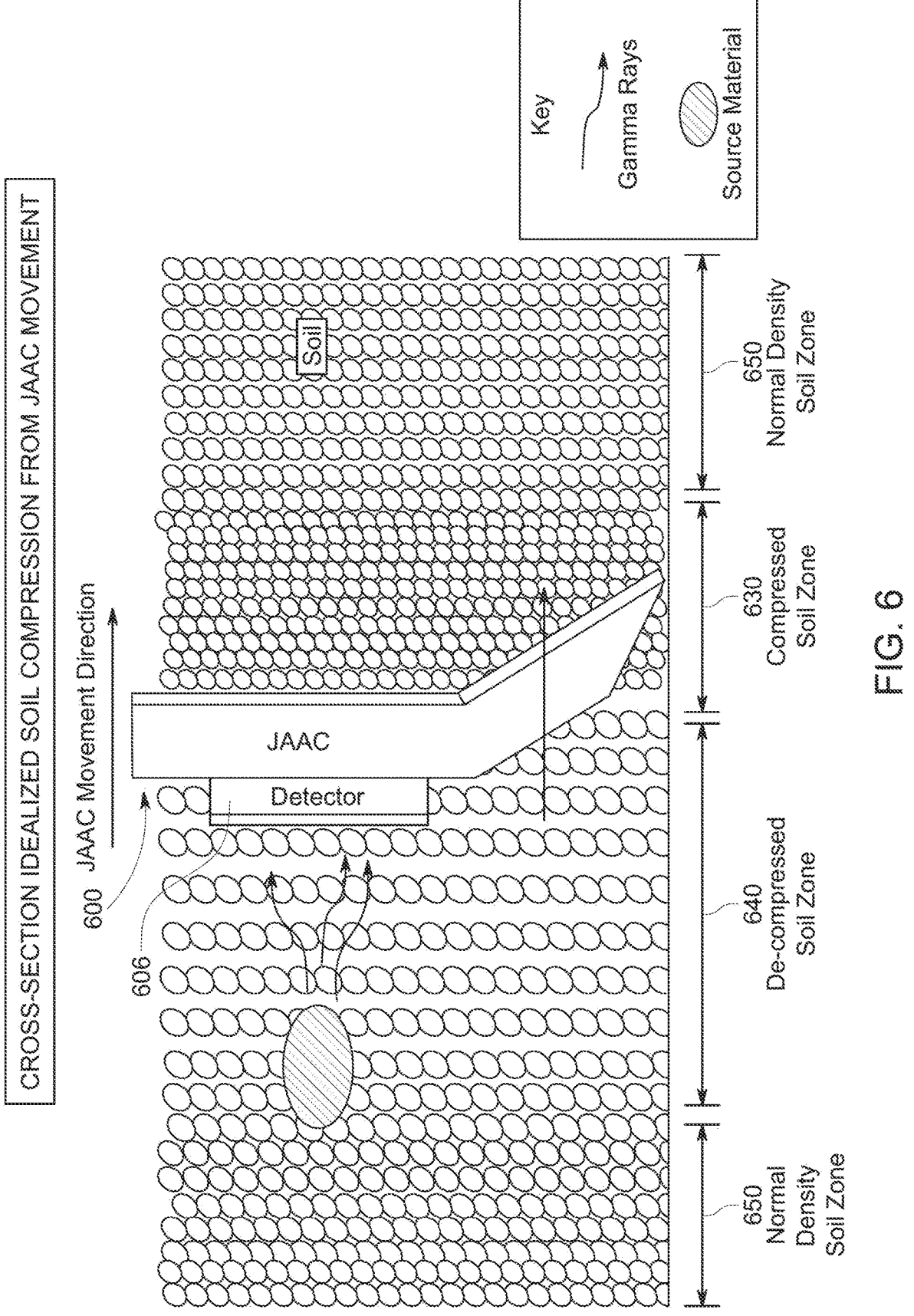
FIG. 6 is a schematic view of the detector enclosure illustrating a protective wrap according to an embodiment.

FIG. 6 is a schematic cross-sectional view of the different soil zones of FIG. 5 as a result of pulling the JAAC through the soil. The JAAC 600 is pulled forward to compress the soil on the leading edge thereby forming the compressed soil zone 630. In the wake of the path of the JAAC 600, the soil becomes de-compressed on the trailing edge of the ripper and anneals in the decompressed soil zone 640. The cross-sectional view shows that in the decompressed soil zone 640, gamma rays have less obstruction and thus are more likely to reach the detector 600. The normal density soil zones 650 are disposed in front of the compressed soil zone 630 and behind the decompressed soil zone 640.

The detector may have a maximum range around the portions of the detector that are unobstructed. However, the JAAC 600 is designed to be pulled by a dozer or an excavator and would be used similar to a plow. The JAAC

600 is designed to protect the subsurface detector 606 from head-on forces created by moving through soil. It is not designed to counteract lateral forces that may occur from turns made by the dozer/JAAC. As such, it is desirable to lift the JAAC out of the soil prior to turning, and then re-insert the JAAC and the detector 606 into the soil to make successive straight runs of the ripper horizontally through the soil. If increases in contamination are detected by JAAC, the recorded GPS position associated with that detection allows for follow-up test pitting or drilling at that location.

FIG. 7 is a flow diagram 700 illustrating an example of a method of subsurface contamination detection. In step 710, a detector is placed inside a detector enclosure which includes a rear-facing side, two lateral-facing sides, and a bottom-facing side. In step 720, a protective wrap is optionally placed between the detector enclosure and the detector to protect the detector from vibration. In step 730, the detector is connected via a cable to a data collecting unit to collect detection data of the detector. In step 740, a front-facing side of the detector enclosure is attached to a ripper of a ripper machine. A variety of attachment mechanisms can be used to attach the detector enclosure to the ripper, including those that are easier and/or faster such as quick-connect mechanisms that do not involve welding. In addition, the cable connection in step 730 may occur after the ripper attachment in step 740.

In step 750, the ripper is inserted into a soil to position the rear-facing side, the two lateral-facing sides, and the bottom-facing side of the detector enclosure below a soil surface of the soil. In step 760, the ripper is moved horizontally through the soil leading with the front-facing side of the detector enclosure to detect subsurface contamination via a rear-facing window using the detector and, optionally, two lateral-facing windows and a bottom-facing window.

At sites where the soil may be contaminated with chemicals, the JAAC can offer an important advantage by minimizing disturbance of subsurface soils. Drilling is still the best way to vertically delineate contamination, but it can be very expensive and time intensive, and is not specifically designed for horizontal delineation. The JAAC is designed to provide a horizontal profile for shallow contamination which can be augmented by vertical investigations.

Successive rows can be surveyed with the JAAC thereby providing shallow coverage to large areas in a small period of time. Comparing the JAAC to traditional technology, a 6-meter borehole might take 2 hours to complete, and a 2-meter-deep trench approximately 5 meters long might also take 2 hours to complete. The initial testing shows that the JAAC is fast, viable, and protective. In an initial test, six runs were made with the JAAC attachment, each about 5 meters long and a maximum depth of about 1.25 meters and the test took 3 minutes. Thus, JAAC has the potential to screen soils at a rate about 2 orders of magnitude faster than traditional subsurface investigations. Additionally, the area encountered by the detector during a pass by the JAAC system may be greater than that using other methods because of the temporary void and lower soil density found behind the moving ripper. Lastly, the initial JAAC trial did not break a thin, fragile glass that was installed inside JAAC; thus, the vibrations of the test were not excessive.

The JAAC is designed to rapidly detect subsurface shallow contamination. Prior approaches are slower and more expensive. For radiological contamination, no system exists for rapidly detecting subsurface radiation without some form of excavation or drilling. Excavation or drilling can be very expensive. It can cause health and safety concerns regarding fugitive emissions and can create contaminated waste that must be properly disposed of. The JAAC can scan subsurface areas with minimal subsurface exposure and waste.

JAAC Initial Test

The USACE decided to initially test JAAC without risking an expensive detector to determine if pulling JAAC through the soil would result in excessive vibrations that would likely destroy sensitive components of a standard NaI detector such as the photo-multiplier tube. A thin fragile wine glass was wrapped in protective bubble wrap and placed inside the enclosure through the hinged door at the base. Ordinary Duct tape was placed over the window so that the glass would not exit the enclosure during the test.

On Nov. 3, 2022 the maiden voyage of JAAC was completed by mounting it to a PC 360 LC Komatsu® excavator. Six total runs were made each approximately 5-meters in length over 3 minutes. In the first run, a small pile of soil about 0.45 meters high was left where the operator removed the ripper. In successive runs, (after settling) a thin strip about 15 cm in height was left, and thus minimal disturbance was encountered.

Although the operator was not specifically instructed to do so, he carefully pulled the JAAC through the soil in a straight line at about the speed of a typical gamma walkover, and instinctively lifted JAAC when an obstruction was encountered. Overall, six runs were made with the JAAC attachment, each about 5 meters long and a maximum depth of about 1.25 meters.

Test Results

Upon completion of 6 runs, the JAAC was returned to the surface and its exterior was grossly decontaminated in accordance with approved site radiological controls and procedures. Surprisingly, most of the duct tape was still in place and had to be removed by the laborers. During the run a void area could be seen behind the trailing edge of JAAC. This was likely due to the changes in the soil density as it passed around the ripper. In the front of the ripper the soil was likely compressed, but as it moved around to the back of the ripper a wake was left behind the ripper. This void might allow the detector to see further into the subsurface. Eventually the soil annealed leaving a very small furrow at the surface. Subsequently, the hatch was opened and the bubble wrap was removed. The fragile glass was removed, unwrapped, and found to be in perfect condition.

A second test was performed in which a fully functioning 2×2 NAI gamma detector, a Ludlum 23221 meter, and a Wi-Fi transmitter were mounted on-board a Komatsu track hoe. Concurrently, the test director had a tablet capable of receiving the live data transmission from the detector (via the Wi-Fi transmitter). The JAAC performed subsurface detection through an area of known radiological contamination. Once JAAC detected radiation, two additional successively deeper runs were made in the area, each showing successively higher counts per minute. After the test runs were made, soil from the location of the highest readings was collected and analyzed from the laboratory. The soil was found to be elevated at 30 pCi/g which was significantly above background uranium levels (generally less than 10 pCi/g) but below the site cleanup levels. This conclusively shows that JAAC can detect low levels of buried radioactive soil.

Conclusions

The initial trial runs of the JAAC contamination detection apparatus showed that the physical stresses from subsurface exploration were low enough to keep a thin fragile glass from breaking; therefore, the technology has been proven to work in a real-world setting. During the initial test, the JAAC traveled at a depth of about 1 meter for a total of 27 meters horizontally in about 3 minutes, which might equate to about 450 meters per hour. At the site, a 6-meter borehole might take 2 hours to complete, and a 2-meter deep trench approximately 5 meters long might also take 2 hours. Thus, the JAAC has the potential to screen soils at a rate about 2 orders of magnitude faster than traditional subsurface radiological investigations. Additionally, the area encountered by the detector in the JAAC system may be greater than other methods because of the ephemeral void and lower soil density found behind the moving ripper. The second trial run included using a NaI detector which conclusively detected gamma radiation at low levels. During that test, data from the subsurface detector was successfully transmitted to an observer with a tablet computer resulting in real-time radioactivity data. That data combined with GPS would provide real-time mapping of subsurface rad data.

In other embodiments, different contamination detectors may be used. For instance, a solid-state cadmium zinc telluride (CZT) detector could be used which, without the need for a photo-multiplier tube, may be less fragile than a more traditional Sodium Iodide (NaI) detector at the cost of a degradation in efficiency and an increase in cost. Longer rippers exist which can extend 2 meters or more into the ground, so that if the successive tests are successful, the JAAC could be deployed on different rippers.

The contamination detection may involve detecting radioactive, volatile organic, Light Non-Aqueous Phase solids (LNAPLs), and certain metal contamination in shallow subsurface areas. Also, the system may be used for geophysical investigations and possibly natural gas leaks.

The JAAC system is the first environmental scanning system to allow detection of contaminants through horizontal movement of a cutlass through soils without substantial disturbance of soils. Vertical drilling and test trenches are commonly used methods, but each is time consuming and creates waste.

The inventive concepts taught by way of the examples discussed above are amenable to modification, rearrangement, and embodiment in several ways. Accordingly, although the present disclosure has been described with reference to specific embodiments and examples, persons skilled in the art will recognize that changes may be made in form and detail without departing from the spirit and scope of the disclosure.

An interpretation under 35 U.S.C. § 112 (f) is desired only where this description and/or the claims use specific terminology historically recognized to invoke the benefit of interpretation, such as "means," and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features and/or methodological steps, it is to be understood that the subject matter defined in the appended claims is not necessarily limited to the specific features or steps described. Rather, the specific features and steps are disclosed as example forms of implementing the claimed subject matter. To the extent headings are used, they are provided for the convenience of the reader and are not to be taken as limiting or restricting the systems, techniques, approaches, methods, devices to those appearing in any section. Rather, the teachings and disclosures herein can be combined, rearranged, with other portions of this disclosure and the knowledge of one of ordinary skill in the art. It is the intention of this disclosure to encompass and include such variation.

The indication of any elements or steps as "optional" does not indicate that all other or any other elements or steps are mandatory. The claims define the invention and form part of the specification. Limitations from the written description are not to be read into the claims.

Embodiments of the invention can be manifest in the form of methods and apparatuses for practicing those methods. As compared to traditional subsurface investigations, the benefits of implementing this technology include detection of contaminants through horizontal movement of a cutlass through soils that would otherwise be undetectable with current technology. Additionally, the JAAC performs detections without substantial disturbance of soils while protecting the detector.

Unless explicitly stated otherwise, each numerical value and range should be interpreted as being approximate as if the word "about" or "approximately" preceded the value or range.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It will be further understood that various changes in the details, materials, and arrangements of the parts which have been described and illustrated in order to explain embodiments of this invention may be made by those skilled in the art without departing from embodiments of the invention encompassed by the following claims.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

All documents mentioned herein are hereby incorporated by reference in their entirety or alternatively to provide the disclosure for which they were specifically relied upon.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

What is claimed is:

1. A contamination detection apparatus for subsurface contamination detection, the contamination detection apparatus comprising:
   a detector enclosure including a front-facing side to be attached to a ripper of a ripper machine and a rear-facing side having a rear-facing window, two lateral-facing sides, and a bottom-facing side; and
   a bottom door at a bottom side of the detector enclosure to move between a closed position and an open position, the bottom door in the closed position supporting a detector to be placed inside the detector enclosure to detect for subsurface contamination via the rear-facing window.

2. The contamination detection apparatus of claim 1, wherein the two lateral-facing sides each have a lateral-facing window and the bottom-facing side has a bottom-facing window.

3. The contamination detection apparatus of claim 1, wherein the detector enclosure comprises a metal box having a size to enclose the detector and at least a portion of a cable connected between the detector and a data collecting unit to collect contamination detection data of the detector.

4. The contamination detection apparatus of claim 1, further comprising:
   a protective wrap disposed between the detector enclosure and the detector to be placed inside the detector enclosure.

5. The contamination detection apparatus of claim 1, further comprising:
   the detector which is a gamma detector;
   the rear-facing window comprises a rear-facing cut-out to facilitate detection of gamma detection by the gamma detector.

6. The contamination detection apparatus of claim 1, further comprising:
   the ripper to which the front-facing side of the detector enclosure is attached.

7. A contamination detection method, comprising:
   attaching a front-facing side of a detector enclosure to a ripper of a ripper machine, the detector enclosure including a rear-facing side having a rear-facing window, two lateral-facing sides, and a bottom-facing side;

placing a detector inside the detector enclosure;

inserting the ripper into a soil to position the rear-facing window, the two lateral-facing sides, and the bottom-facing side of the detector enclosure below a soil surface of the soil; and moving the ripper horizontally through the soil leading with the front-facing side of the detector enclosure to detect subsurface contamination via the rear-facing window using the detector.

8. The contamination detection method of claim 7, wherein the two lateral-facing sides each have a lateral-facing window and the bottom-facing side has a bottom-facing window, and wherein moving the ripper comprises:

moving the ripper horizontally through the soil leading with the front-facing side of the detector enclosure to detect subsurface contamination via the rear-facing window, the lateral-facing windows, and the bottom-facing window using the detector.

9. The contamination detection method of claim 7, wherein placing the detector inside the detector enclosure comprises:

moving a bottom door at a bottom side of the detector enclosure to an open position, inserting the detector into the detector enclosure via the bottom side, and moving the bottom door to a closed position supporting the detector to detect for subsurface contamination via the rear-facing window.

10. The contamination detection method of claim 7, further comprising:

connecting the detector via a cable to a data collecting unit to collect subsurface contamination detection data of the detector, the detector enclosure enclosing at least a portion of the cable which is below the soil surface of the soil.

11. The contamination detection method of claim 7, further comprising:

placing a protective wrap between the detector enclosure and the detector to cushion the detector.

12. The contamination detection method of claim 7, further comprising:

performing gamma radiation detection of the soil using the detector via the rear-facing window of the detector enclosure.

13. The contamination detection method of claim 7, wherein the two lateral-facing sides each have a lateral-facing window and the bottom-facing side has a bottom-facing window, the contamination detection method further comprising:

performing gamma radiation detection of the soil using the detector via the rear-facing window, the lateral-facing windows, and the bottom-facing window of the detector enclosure.

14. The contamination detection method of claim 7, further comprising:

moving the ripper horizontally through the soil to compress the soil on the front-facing side of the detector enclosure, to divide the soil on two sides of the ripper, and to decompress and anneal the soil on the rear-facing side of the detector enclosure, to detect for subsurface contamination of the soil which is decompressed and annealed via the rear-facing window using the detector.

15. The contamination detection method of claim 14, further comprising:

lifting the ripper and the detector enclosure out of the soil prior to turning the ripper and the detector enclosure and re-insert the ripper and the detector enclosure into the soil to make straight runs of the ripper horizontally through the soil.

16. A contamination detection apparatus for subsurface contamination detection, the contamination detection apparatus comprising:

a ripper of a ripper machine; and a detector enclosure including a front-facing side to be attached to the ripper of the ripper machine and a rear-facing side having a rear-facing window, two lateral-facing sides, and a bottom-facing side;

the rear-facing side of the detector enclosure including a rear-facing window to facilitate detection, by a detector disposed inside the detector enclosure, for subsurface contamination via the rear-facing window.

17. The contamination detection apparatus of claim 16, wherein the two lateral-facing sides each have a lateral-facing window and the bottom-facing side has a bottom-facing window.

18. The contamination detection apparatus of claim 16, further comprising:

a protective wrap disposed between the detector enclosure and the detector to be placed inside the detector enclosure.

19. The contamination detection apparatus of claim 16, wherein the detector which is a gamma detector;

the rear-facing window comprises a rear-facing cut-out to facilitate detection of gamma detection by the gamma detector.

20. The contamination detection apparatus of claim 16, wherein the detector which is a gamma detector;

the rear-facing window is covered with a plastic sheet through which gamma radiation can pass to facilitate detection of gamma detection by the gamma detector.

\* \* \* \* \*